United States Patent
Jirkovsky et al.

(10) Patent No.: US 7,256,289 B2
(45) Date of Patent: Aug. 14, 2007

(54) PROCESS FOR MAKING CHIRAL 1,4-DISUBSTITUTED PIPERAZINES

(75) Inventors: Ivo Ladislav Jirkovsky, Waitsfield, VT (US); Joseph Zeldis, New City, NY (US); Gregg Brian Feigelson, Chester, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/147,055

(22) Filed: Jun. 7, 2005

(65) Prior Publication Data

US 2005/0228181 A1 Oct. 13, 2005

Related U.S. Application Data

(62) Division of application No. 10/384,837, filed on Mar. 10, 2003, now Pat. No. 7,019,137.

(60) Provisional application No. 60/363,458, filed on Mar. 12, 2002.

(51) Int. Cl.
*C07D 405/04* (2006.01)
(52) U.S. Cl. ............... 544/377; 544/377; 544/394; 560/172
(58) Field of Classification Search ............... 544/377
See application file for complete search history.

(56) References Cited

U.S. PATENT DOCUMENTS

| | | | |
|---|---|---|---|
| 5,424,313 A | 6/1995 | Hertog et al. | |
| 5,889,010 A * | 3/1999 | Faraci et al. | 514/253.06 |
| 6,127,357 A | 10/2000 | Cliffe et al. | |
| 6,271,234 B1 | 8/2001 | Leonardi et al. | |
| 6,713,626 B2 * | 3/2004 | Feigelson et al. | 544/360 |
| 6,784,294 B2 | 8/2004 | Chan et al. | |
| 7,019,137 B2 | 3/2006 | Jirkovsky et al. | |
| 7,091,349 B2 | 8/2006 | Feigelson et al. | |
| 2004/0230056 A1* | 11/2004 | Feigelson et al. | 544/360 |

FOREIGN PATENT DOCUMENTS

| | | |
|---|---|---|
| JP | 01125357 A2 | 5/1989 |
| WO | WO93/22303 A1 | 11/1993 |
| WO | WO94/24115 | 10/1994 |
| WO | WO95/33725 | 12/1995 |
| WO | WO95/33743 | 12/1995 |
| WO | WO-9601656 | 1/1996 |
| WO | WO97/03982 | 2/1997 |
| WO | WO97/37655 | 10/1997 |
| WO | WO-0244142 | 6/2002 |

OTHER PUBLICATIONS

Kagayaki Natsuka et al., J. Med. Chem., 1987, 1779-1787, 30.
Frank Kerrigan et al., Tetrahedron Letters, 1998, 2219-2222, 39.
Sheryl J. Hays, J. Labelled Compounds and Radiopharmaceuticals, 1986, 351, 24(4).
Jean-Louis Peglion et al., J. Med. Chem., 1995, 4044-4055, 38.
Shawn J. Stachel et al., Tetrahedron Letters, 1999, 5811-5812, 40.
Julian M.C. Golec et al., Bioorganic & Medicinal Chemistry Letters, 1997, 2181-2186, 7(17).
Dan Muller, J. Org. Chem., 1997, 411-416, 62.
G. Mark Taylor et al., Tetrahedron Letters, 1996, 1297-1300, 37(8).
Database Crossfire Beilstein, Reg. No. 3915193.
Database Crossfire Beilstein, Reg. No. 1512459.
Zoltan Zubovics, Eur. J. Med. Chem., 1986, 370-378, 21(5).
G. Cignarella et al., Il Farmaco—Ed. Sc., 1976, p. 194, 196, v. 31.
Lee T. Boulton, J. Chem. Soc., Perkin Trans. 1, 1999, 1421-1429.
G. Cignarella, Il Farmaco—Ed. Sc., 1976, 194-200, 31(3).
Ulrike Burkard et al., Chem. Ber., 1986, 1594-1612, 119.
Wincenty Kwapiszewski et al., Acat Pol. Pharm., 1999, 41-47, 56(1) (Abstract).
Michimasa Izumi et al., Chem. and Pharm. Bull. (Japan), 1954, 275-279, 2(3).
Isao Aiko et al., Chem. and Pharm. Bull. (Japan), 1957, 487-488, 5(5).
Syed M. Quadri et al., Bioorganic & Medicinal Chemistry Letters, 1992, 1661-1664, 2(12).
Robert V. Hoffman et al., Tetrahedron Letters, 1990, 2953-2956, 31(21).
Sandrine Marchais et al., Bioorganic & Medicinal Chemistry, 2001, 695-702, 9.

* cited by examiner

*Primary Examiner*—Emily Bernhardt
(74) *Attorney, Agent, or Firm*—Wilmer Cutler Pickering Hale and Dorr LLP

(57) ABSTRACT

A process for a stereoselective preparation of novel chiral nitrogen mustard derivatives useful in synthesizing optically active 1,4-disubstituted piperazines of formula:

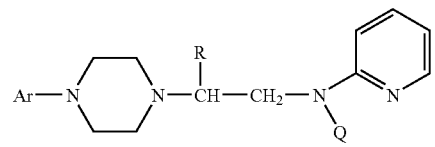

wherein R, Ar, and Q are defined as set forth herein, and intermediate compounds therefor. The 1,4-disubstituted piperazines act as 5HT1A receptor binding agents useful in the treatment of Central Nervous System (CNS) disorders. The intermediate compounds of Formula II and IV as set forth herein are also included.

3 Claims, No Drawings

PROCESS FOR MAKING CHIRAL 1,4-DISUBSTITUTED PIPERAZINES

This application is a divisional of application Ser. No. 10/384,837, filed on Mar. 10, 2003, now U.S. Pat. No. 7,019,137 which claims priority from provisional application Ser No. 60/363,458, filed on Mar. 12, 2002, the entire disclosure of which is hereby incorporated by reference.

BACKGROUND OF THE INVENTION

Piperazines of formula A

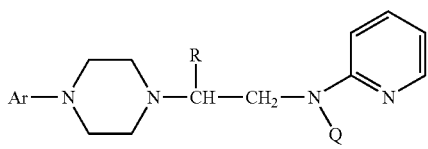

wherein R is a lower alkyl, Ar is an unsubstituted or substituted aryl or heteroaryl, and Q is a hydrogen, CO-(lower) alkyl, CO-cycloalkyl, or CO-aryl, are potent 5HT1A receptor binding agents. U.S. Pat. No. 6,127,357 teaches such piperazine derivatives that are useful in the treatment of Central Nervous System (CNS) disorders. Piperazine derivatives of formula A contain an asymmetric carbon so they may exist in two optically active forms. It is now well understood that enantiomers bind to receptors with different potency and selectivity, they may have different metabolic fate and produce different side effects. WO 9703982 teaches that preferred enantiomers of piperazines of formula A display improved 5HT1A binding affinity and bioavalability. Therefore, an efficient, operationally facile, inexpensive and safe alternative process for making these homochiral piperazines is desirable.

WO 9533725 teaches a method for synthesizing some chiral piperazines of formula A by alkylation of the corresponding 1-aryl-piperazine with enantiomerically pure 2-(5-methyl-2,2-dioxido-1,2,3-oxathiazolidin-3-yl)pyridine.

One conventional approach to creating 1,4-disubstituted piperazines is via bis-alkylation of primary amines with bis(2-chloroethyl) amines, the so-called nitrogen mustard gases. A few optically active piperazines, structurally unrelated to formula A, have been prepared by condensation of an N-substituted bis(2-chloro-ethyl)amine with a selected chiral amine according to Natsuka et al. in J.Med.Chem. 1987, 1779 and WO 9424115, and with a natural amino acid according to Acta Pol.Pharm.1999, 56, p. 41; CA 131: 157745. However, there is a need for a process to make synthetically useful, chiral nitrogen mustard molecules. Chem.& Pharm.Bulletin Japan 1954, 275 describes a conversion of bis(2-chloroethyl)amine into N-bis(2-chloroethyl) aminoacetonitrile, and a related paper in Chem.& Pharm.Bulletin Japan 1957, 487 reports an unsuccessful attempt to resolve the corresponding racemic N-bis(2-chloroethyl)alanine, and tedious resolution of 2-[N-bis(2-chloro-ethyl)amino]propanamide.

Polyfunctional chiral amines are accessible by several multi-step procedures, but a direct displacement of a reactive functional group typically results in racemic amines.

Effenberger et al. (Angew.Chem. 1983, 95[1], 50) reported that triflates react with simple secondary amines under Walden inversion. This process was applied to the syntheses of both (R)- and (S)-α-amino acid esters. The method allows asymmetric formation of C(α),N-bond in a single reaction with a high degree of stereoselectivity, and has been occasionally used with minor modifications (Quadri et al., Biorg.&Med.Chem.Letters 2, 1661, 1992; Taylor et al., Tetrahedron Letters 37, 1297, 1996). Hoffman and Hwa-Ok Kim, Tetrahedron Letters 31, 2953, 1990 replaced triflates with (4-nitrobenzene)sulfonyloxy esters in a reaction with hydrazines.

SUMMARY OF THE INVENTION

The present invention comprises a process for the preparation of a compound of formula III

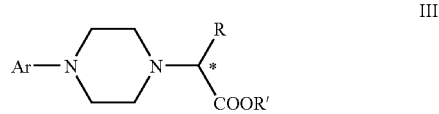

wherein R and R' each independently represents a $C_1$–$C_3$ alkyl group; Ar represents a dihydrobenzodioxinyl or benzodioxinyl, or phenyl optionally substituted with up to three substituents independently selected from halogen, methoxy, halomethyl, dihalomethyl and trihalomethyl;

said process comprising reacting a compound of formula Ia and a compound of formula Ib to form a compound of formula II,

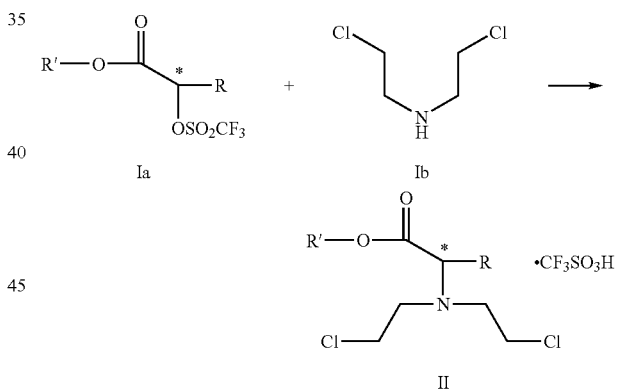

and further reacting the compound of formula II with an aryl amine compound, Ar—$NH_2$, in which Ar is defined as stated above, to produce a compound of formula III. Preferably, these steps are performed in a concatenated manner to form compound III without isolating intermediate compound II.

In a preferred embodiment, the compound of formula Ia is a single enantiomer, (S) or (R), that leads to the formation of a single enantiomer of a compound of formula II having an inverted configuration, i.e. (R) or (S). Hydride reduction of compound of formula III then proceeds with retention of configuration to form the intermediate compound of formula IV.

The invention further comprises the reaction of a compound of formula IV to form the intermediate compounds of formulae V:

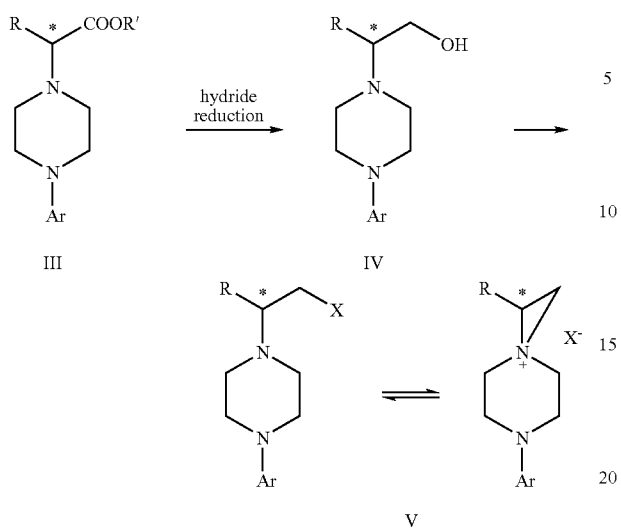

III → IV

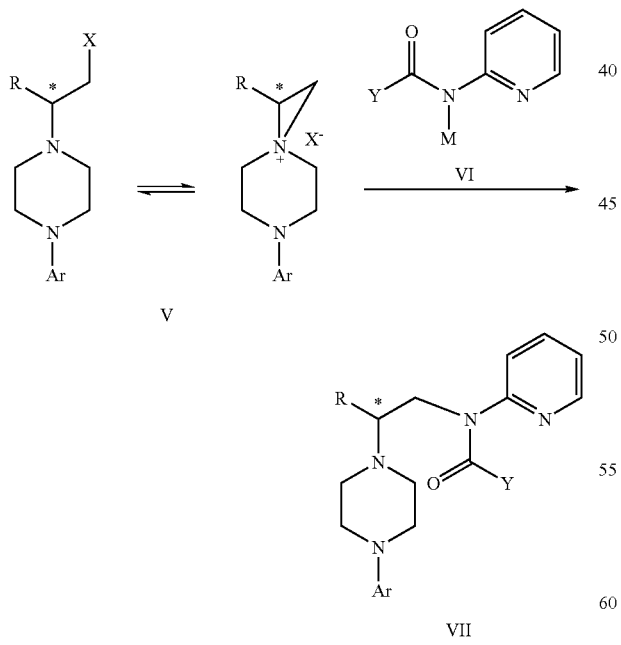

V where X is a leaving group such as halo (especially chloro and bromo), methansulfonyloxy, p-toluenesulfonyloxy, or p-bromophenylsulfonyloxy.

The invention also comprises the novel compounds represented by formulae II, III, IV and V, and the optical isomers thereof.

The invention also comprises the following process steps, in which compound V is used to make compounds VII, VIII and IX:

treating the compound of formula V with a compound of formula VI in an aprotic solvent wherein M is an alkali metal (e.g., Na, Li, K) and Y represents a moiety selected from the group consisting of $C_1$–$C_6$ alkoxy, $C_1$–$C_6$ alkyl, $C_3$–$C_7$ cycloalkyl and $C_3$–$C_7$ cycloalkoxy;

treating the compound of formula VII with a protic acid to form a compound of formula VIII

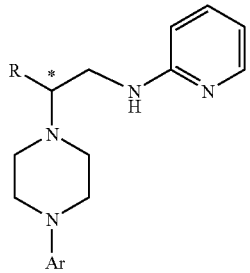

VIII and, treating the compound of formula VIII with an aroyl compound selected from aroyl chloride, aroyl bromide and aroyl anhydride, in the presence of a base, to form a compound of formula IX

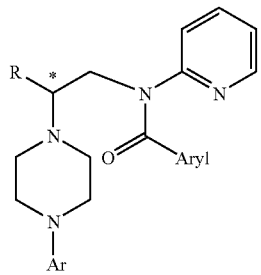

IX wherein Aryl represents a $C_6$–$C_{12}$ aromatic group optionally substituted with up to three substituents independently selected from the group consisting of halogen atoms, alkyl, alkoxy, alkoxycarbonyl, nitro, amino, alkylamino, dialkylamino, haloalkyl, dihaloalkyl, trihaloalkyl, nitrile and amido substituents each having no more than six carbon atoms.

DETAILED DESCRIPTION

The present invention provides a process for preparing specific enantiomeric compounds as intermediates in the formation of 1,4-disubstituted piperazines that are useful as serotonin 1A receptor-binding agents. Chiral nitrogen mustard derivatives serve as primary reactants. This process results in a simpler reaction sequence than was previously known. The novel synthesis of chiral 1,4-disubstituted piperazines generates storage stable, synthetic intermediates for compounds of formula IX, shown above.

Various aspects of a preferred embodiment of the present invention are shown in Scheme 1:

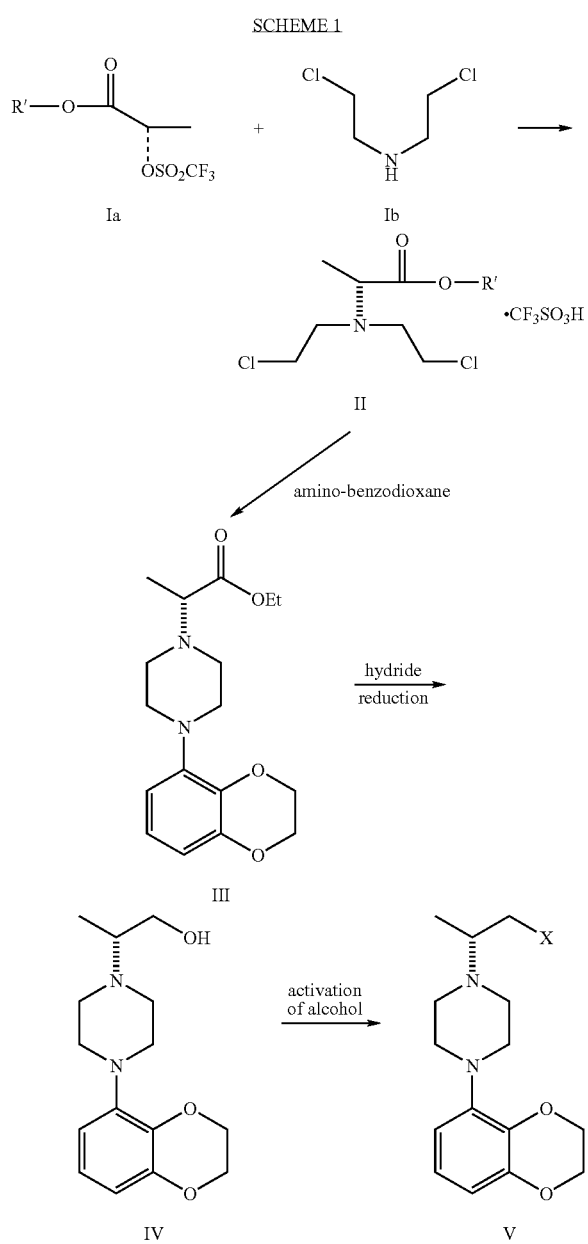

Referring to Scheme 1, (S)-2-[(trifluoromethylsulfonyl)oxy]propionate is commercially available, or such lactate triflates can be readily prepared from the corresponding alkyl lactates, for example according to the procedures of Prasad et al., J.Chem.Soc.Perkin Trans I, 1991, 3331, and Wang and Xu, Tetrahedron 54, 12597, 1998. Bis(2-chloroethyl)amine is liberated as a free base from its hydrochloride salt. The reaction of the first step in Scheme 1 is conducted in an inert organic solvent in which the starting materials are soluble, such as tetrahydrofuran, dioxane, 1,2-dimethoxyethane, diethyl ether, tert-butyl methyl ether, methylene chloride, chlorobenzene, trifluoromethylbenzene, or toluene. The temperature is not critical, and suitably may be from 0° C. to about 50° C., preferably between ice-bath and room temperature. Higher temperatures promote an undesirable elimination process. The reaction is generally run for 4–6 hours, although prolonged stirring times of up to 18–24 hours are not detrimental. Yields of the corresponding compound of formula II may be as high as 83%, but more typically, yields are in the range of 50–65%. Tetrahydrofuran is an optimum solvent, however, it is very sensitive to the presence of traces of triflic acid or triflic anhydride that may initiate partial tetrahydrofuran polymerization, and the resulting gelatinous material complicates isolation of the product.

A preferred embodiment of this invention comprises a one-step process wherein compound II is prepared in chlorobenzene as a crystalline triflic salt and is used to alkylate 2,3-dihydro-1,4-benzodioxin-5-amine in chlorobenzene to form compound III. The compound of formula II may be reacted with 2,3-dihydro-1,4-benzodioxin-5-amine in refluxing chlorobenzene for a period about 8 to about 18 hours. The formation of the compound of formula III thus may be effected in a concatenated manner by using a chlorobenzene solvent and continuing without a necessity for interim isolation of the compound of formula II.

An aminoester of the compound of formula III can be isolated as a free base or converted to a stable hydrochloride salt. Alternatively, the compound of formula III is obtained by condensation of 2,3-dihydro-1,4-benzodioxin-5-amine with a free base of compound of formula II under similar conditions, and both intermediates II and III are used in a crude state in the subsequent steps.

A preferred embodiment for formation of the compound of formula III from the compound of formula II comprises the reaction with amino-benzodioxine as illustrated in Scheme I. In another embodiment of this invention, an amino-phenyl is used instead of the amino-benzodioxane, wherein the phenyl may be substituted with up to three substituents independently selected from halogen, methoxy, halomethyl, dihalomethyl and trihalomethyl.

Intermediates of the compound of formula III can be reduced to the alcohol of formula IV by the use of reducing agents. The reaction is performed by conventional methods well known to those skilled in art, for example by using a complex metal hydride or a boron reducing agent under non-epimerizing conditions.

In a preferred embodiment of the process of this invention, the reduction is carried out under reflux in ether or in tetrahydrofuran at 20–40° C., using lithium aluminum hydride. The enantiomeric purity of the isolated alcohol IV is 98% or greater, as determined on a chiral column using a sample of racemic IV as reference.

In a further aspect of this invention, the alcohol of the compound of formula IV may be treated with methanesulfonyl chloride in the presence of an organic base in methylene chloride to produce the intermediate compound of formula V. In an alternative embodiment, the alcohol of formula V or its hydrochloride salt is heated with thionyl chloride in refluxing chloroform to obtain a hydrochloride salt of the compound of formula V.

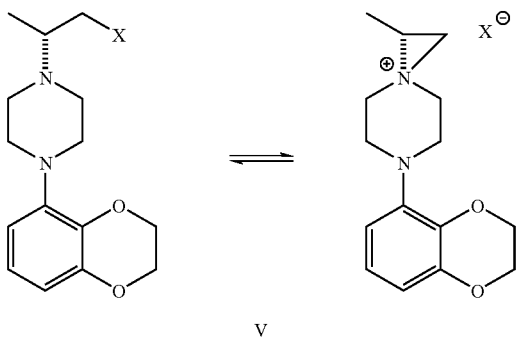

V

Depending on the nature of the leaving group X, acidity of the medium, concentration, or solvent polarity, these piperazines may exist in an equilibrium with 6-aza-3-azoniaspiro[2,5] octane species.

The present invention further comprises the novel compounds of formula II, III, and IV. Preferred embodiments thereof include:

N,N-bis(2-chloroethyl)-(R)-alanine methyl ester, trifluoromethanesulfonate;
N,N-bis(2-chloroethyl)-(R)-alanine ethyl ester, trifluoromethanesulfonate;
(R)-4-(2,3-dihydro-1,4-benzodioxin-5-yl)-α-methyl-1-piperazineacetic acid ethyl ester;
(R)-4-(2,3-dihydro-1,4-benzodioxin-5-yl)-α-ethyl-1-piperazineacetic acid ethyl ester;
(R)-4-(2,3-dihydro-1,4-benzodioxin-5-yl)-α-methyl-1-piperazineacetic acid methyl ester;
(R)-4-(2,3-dihydro-1,4-benzodioxin-5-yl)-α-ethyl-1-piperazineacetic acid methyl ester;
(R)-4-(2,3-dihydro-1,4-benzodioxin-5-yl)-β-methyl-1-piperazineethanol; and,
(R)-4-(2,3-dihydro-1,4-benzodioxin-5-yl)-β-ethyl-1-piperazineethanol.

Compound V can be reacted with a compound of formula VI to form a compound of formula VII. Y represents a moiety selected from the group consisting of $C_1$–$C_6$ alkoxy, $C_1$–$C_6$ alkyl, $C_3$–$C_7$ cycloalkyl and $C_3$–$C_7$ cycloalkoxy.

The aminopyridyl functionality is introduced via displacement. It is not apparent from the prior art how seriously the side reactions described above can threaten the usefulness of this displacement. Much depends on the specific alkylating reagent. In WO9703982, an aminopyridine VIa, under unspecified conditions, can be treated with generic compounds Va, where X is a leaving group, to give VIIa. In the course of developing this invention, we have observed that the anion of N-alkanoyl compounds (i.e., VIb) reacts with V (X=Cl) to give a significant quantity (ca. 20%) of undesired alkylation on the pyridyl nitrogen, forming compound X. In a preferred embodiment of the present invention, Y is an alkoxy group, more preferably $C_1$–$C_6$ alkoxy.

This invention provides a practical synthesis of N-aryl piperazines where chirality is introduced at the piperazine ring formation step and 2-aminopyridyl substitution is incorporated via displacement.

The use of t-Boc 2-amino pyridine, VI, as described in this invention significantly suppresses the amount (<7%) of analogous by-product formed, increasing the proportion of desired compound VII. As shown in the preceding section, the t-Boc protecting group is easily removed and the freed amine can be then acylated.

Throughout this specification and in the appended claims, except where otherwise indicated, the terms halogen and halo refer to F, Cl and Br, and the terms alkyl, alkane, alkanol and alkoxy include both straight and branched chain alkyl groups.

The following examples are presented to illustrate certain embodiments of the present invention, but should not be construed as limiting the scope of this invention.

EXAMPLE I

N,N-Bis(2-chloroethyl)-(R)-alanine ethyl ester, trifluoromethanesulfonate

A suspension of bis(2-chloroethyl)amine hydrochloride (0.392 g; 2.1 mmol) in 5N aqueous sodium hydroxide (3 mL) is extracted with ether (2×10 mL) and the combined extracts are washed with a minimum amount of water and saturated brine. The ethereal solution is dried quickly over magnesium sulfate and filtered. Tetrahydrofuran (2 mL) is

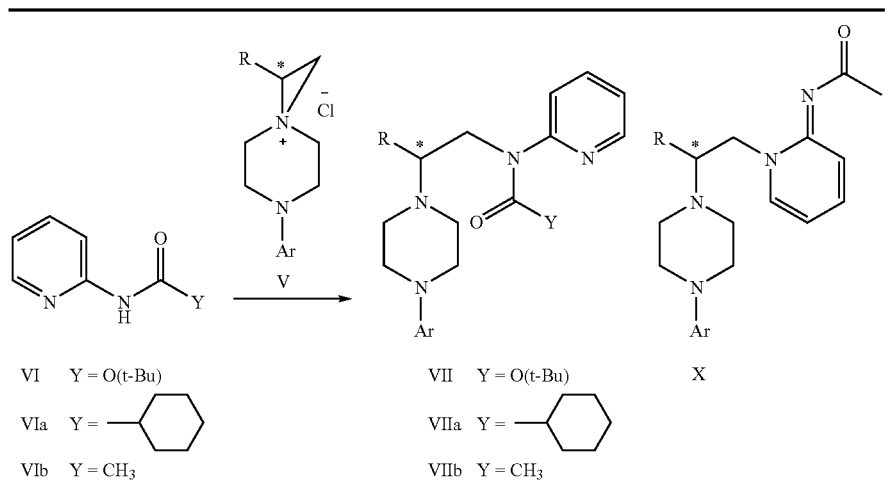

| VI | Y = O(t-Bu) | VII | Y = O(t-Bu) | X |
| VIa | Y = —⬡ | VIIa | Y = —⬡ | |
| VIb | Y = CH₃ | VIIb | Y = CH₃ | | added to the filtrate, and ether is carefully removed under reduced pressure on a rotavapor unit without heating. The residue is mixed with a solution of ethyl (S)-2-[(trifluoromethylsulfonyl)oxy]-propionate (0.5 g; 2 mmol) in tetrahydrofuran (1 mL). After stirring the reaction mixture for 24 hrs at room temperature, there is no visible precipitate. The volatiles are removed under reduced pressure and the remaining viscous oil is dissolved in ether (8 mL), and the slightly turbid solution is filtered after 60 minutes. The filtrate is treated dropwise with n-heptane to induce crystallization; the final ratio of n-heptane/ether is 1:3. The crystalline salt is collected by filtration and washed quickly with a small portion of ether. There is obtained 0.653 g (yield 83.3%) of N,N-bis(2-chloroethyl)-(R)-alanine ethyl ester, trifluoromethanesulfonate; mp 73–74.5° C.; $^1$H NMR (300 MHz, CDCl$_3$) δ 1.35 (t, J=7.1 Hz, 3H), 1.76 (d, J=7.2 Hz, 3H), 3.87 (m, 2H), 4.00 (m, 2H), 4.35 (q, J=7.1 Hz, 2H), 4.57 (q, J=7.2 Hz, 1H), 9.02 (b, 1H).

EXAMPLE II (R)-4-(2,3-Dihydro-1,4-benzodioxin-5-yl)-α-methyl-1-piperazineacetic acid ethyl ester A solution of 2,3-dihydro-1,4-benzodioxin-5-amine (0.327 g; 2.16 mmol) in chlorobenzene (2 mL) is added to a solution of N,N-bis(2-chloroethyl)-(R)-alanine ethyl ester (trifluoromethanesulfonic acid salt; 0.850 g; 2.16 mmol) in the same solvent (2 mL). The stirred reaction mixture is heated at 130° C. for 15 hours, the volatiles are removed on a rotavap, and the semi-solid residue is partitioned between 10% sodium bicarbonate (15 mL) and ether. Organic extracts are washed with brine, dried over magnesium sulfate, and filtered. TLC (chloroform) shows formation of a new product with $R_F$ 0.15, (R)-4-(2,3-dihydro-1,4-benzodioxin-5-yl)-α-methyl-1-piperazineacetic acid ethyl ester. Upon addition of 1N ethereal HCl, (R)-4-(2,3-dihydro-1,4-benzodioxin-5-yl)-α-methyl-1-piperazineacetic acid ethyl ester is converted into its hydrochloride salt that is collected by filtration; 0.615 g (80%), mp 168–171° C. The salt can be recrystallized from ethanol-ether, or acetone-ether. $^1$H NMR (300 MHz, DMSO-d$_6$) δ 1.25 (t, J=7.1 Hz, 3H), 1.58 (d, J=7.2 Hz, 3H), 3.16 (m, 2H), 3.36 (m, 2H), 4.23 (m, 4H), 4.26–4.38 (m, 3H), 4.48 (b, 4H), 6.52 (d, J=7.9 Hz, 1H), 6.57 (d, J=8 Hz, 1H), 6.76 (t, J=8 Hz, 1H), 11.3 (b, <1H).

EXAMPLE III (R)-4-(2,3-Dihydro-1,4-benzodioxin-5-yl)-β-methyl-1-piperazineethanol The hydrochloride salt made by Example II (1.07 g; 3 mmol) is suspended in 5% aqueous sodium bicarbonate (6 mL) and extracted with ether. The organic phase is separated, washed with brine, dried quickly over magnesium sulfate and filtered. The filtrate is added to a stirred suspension of lithium aluminum hydride (0.34 g; 9 eq) and the mixture is heated to a mild reflux for 3 hours. After cooling, it is decomposed with water (1 mL) and 0.5N hydrochloric acid (7 mL). The aqueous layer is separated, basified with 10% sodium bicarbonate and re-extracted with ether. The combined extracts are washed with small amounts of water and brine, dried over magnesium sulfate, filtered and evaporated. The oily product (0.69 g; yield 82%) slowly crystallizes upon standing, and can be recrystallized from n-butanol/n-heptane; mp 92° C.; enantiomeric purity 98%; $^1$H NMR (300 MHz, CDCl$_3$) δ 1.03 (d, J=7 Hz, 3H), 2.74 (m,2H), 2.97 (m, 3H), 3.14 (m, 4H), 3.42 (t, J=11 Hz, 1H), 3.57 (dd, J=11 Hz, J$_1$=5Hz, 1H), 4.35 (sym m, 4H), 6.53 (d, J=7.9 Hz, 1H), 6.61 (d, J=7.9 Hz, 1H), 6.75 (t, J=7.9 Hz, 1H)

EXAMPLE IV (R)-4-(2,3-Dihydro-1,4-benzodioxin-5-yl)-α-methyl-1-piperazineacetic acid ethyl ester A free base of bis(2-chloroethyl)amine is liberated by partitioning its hydrochloride salt between 5N aqueous sodium hydroxide and methylene chloride, in an analogous manner to that used for Example I. The isolated bis(2-chloroethyl)amine (0.94 g; 6.56 mmol) is then added in two portions over 1 hour into a stirred solution of (S)-2-[(trifluoromethylsulfonyl)oxy] propionate (0.82 g; 3.28 mmol) in chlorobenzene (10 mL) at room temperature. The reaction mixture is stirred for additional 2 hours, the solid precipitate is filtered off and washed with a small volume of chlorobenzene. The filtrate is mixed with a solution of 2,3-dihydro-1,4-benzodioxin-5-amine (0.46 g; 3 mmol) and the reaction mixture is heated to reflux for 18 hours. After cooling, the product is rendered basic with 5% aqueous sodium bicarbonate (20 mL) and extracted twice with ether (50 mL). The combined extracts are washed with water, brine, dried over magnesium sulfate, and filtered. The filtrate is concentrated in vacuo to give a crude product that can be directly reduced, or passed through a plug of silica gel in chloroform to obtain compound III (0.49 g; overall yield 50%). The material is identical to that described in Example II.

EXAMPLE V (R)-4-(2,3-Dihydro-1,4-benzodioxin-5-yl)-β-methyl-1-piperazineethanol

A free base of bis(2-chloroethyl)amine (28.4 g; 0.2 mol) is liberated from its hydrochloride salt as described in Example IV and mixed with a solution of (S)-2-[(trifluoromethylsulfonyl)oxy] propionate (20 g; 0.08 mol) in chlorobenzene (150 mL). The mixture is stirred for 3 hours at room temperature, and the resulting thick slurry is washed with water (100 mL) and 10% sodium bicarbonate (100 mL). The organic phase is transferred to a flask containing 2,3-dihydro-1,4-benzodioxin-5-amine (9.6 g; 0.064 mol) and the reaction mixture is allowed to reflux upon stirring for 18 hours. A small amount of yellow precipitate appears. The mixture is cooled to room temperature and agitated with 10% aqueous sodium bicarbonate (55 mL) for 1 hour. The organic layer is separated, dried over sodium sulfate, filtered, and concentrated in vacuo. The residue is dissolved in tetrahydrofuran (50 mL) and added dropwise to a stirred suspension of lithium aluminum hydride (9.1 g; 0.24 mol) in tetrahydrofuran (50 mL). The mixture is heated to 40° C. for 90 minutes, cooled, and decomposed by dropwise addition of ethyl acetate (200 mL). The product is then extracted with 2N hydrochloric acid (500 mL), the aqueous portion is washed three times with ethyl acetate (150 mL) and rendered basic with 10N sodium hydroxide to re-extract the product with ethyl acetate (2×200 mL). The combined extracts are washed with brine, dried over sodium sulfate, filtered and evaporated in vacuo. The residual oil crystallizes upon standing, and in TLC analysis (ethyl acetate-hexane 3:2) co-spots with the alcohol of Example III. Spectroscopic data and enantiomeric purity are identical to those presented in Example III. Overall yield 9.1 g (51%) based on 2,3-dihydro-1,4-benzodioxin-5-amine.

EXAMPLE VI

6-(2,3-Dihydro-1,4-benzodioxin-5-yl)-1-methyl-6-aza-3-azoniaspiro[2,5]octane chloride A solution of the alcohol made according to Example III (0.5 g: 1.8 mmol) in methylene chloride (15 mL) is treated with triethylamine (0.2 g; 1.98 mmol). The mixture is stirred on a ice bath and a solution of methanesulfonyl chloride (0.24 g; 2.1 mmol) in methylene chloride (2 mL) is added dropwise. After 20 minutes, the ice bath is removed, and the reaction mixture is kept at room temperature overnight. The resulting solution is washed successively with a small amount of water, 5% aqueous sodium bicarbonate, and brine, then dried over magnesium sulfate and filtered. The volatiles are removed on a rotavap to give an oily product (0.5 g). $^1$H NMR (300 MHz, CDCl$_3$) δ 1.55 (d, J=7.2 Hz, 3H), 2.54 (dd, J=15 Hz, J$_1$=7.5 Hz, 1H), 2.64–2.81 (m, 5H), 3.11 (m, 4H), 4.11 (sym m, 1H), 4.27 (m, 4H), 6.52 (d, J=7.8 Hz, 1H), 6.57 (d, J=8 Hz, 1H), 6.76 (t, J=7.8 Hz, 1H)

EXAMPLE VII

(R)-4-(2,3-Dihydro-1,4-benzodioxin-5-yl)-1-(2-chloro-1-methylethyl)piperazine A solution of the alcohol made according to Example III (0.3 g: 1.08 mmol) in methylene chloride (5 mL) is acidified with ethereal HCl, the resulting solution is evaporated, and the semi-crystalline residue triturated with ether. After decanting, the material is crystallized from acetonitrile-ether, mp 207–210° C. This salt (0.35 g) is suspended in chloroform (6 mL), thionyl chloride (0.2 g) is added, and the mixture is subjected to reflux for 8 hours. The resulting solution is allowed to cool, volatiles are removed in vacuo, and the residue is stripped with toluene and dried. TLC (ethyl acetate-hexane 3:2) shows no alcohol starting material present. $^1$H NMR (300 MHz, DMSO-d$_6$) δ 1.56 (d, J=7 Hz, 3H), 3.45 (m, 6H), 4.64 (m, 2H), 4.75 (m,1H); the spectrum also shows the presence of the aziridinium species. The product can be used directly for alkylation of 2-(tert-butoxy-carbonyl-amino) pyridine.

Many variations of the present invention not illustrated herein will occur to those skilled in the art. The present invention is not limited to the embodiments illustrate and described herein, but encompasses all the subject matter within the scope of the appended claims and equivalents thereof.

What is claimed is:

1. A compound of formula IV

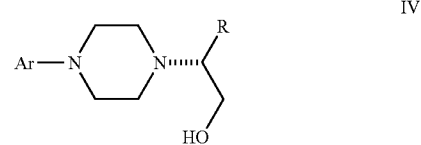

wherein R is C1–C3-alkyl and Ar represents dihydro-benzodioxinyl or benzodioxinyl, and the optical isomers thereof.

2. A compound according to claim 1 wherein Ar represents 2,3-dihydro-benzodioxin-5-yl.

3. A compound selected from the group consisting of
(R)-4-(2,3-dihydro-1,4-benzodioxin-5-yl)-β-methyl-1-piperazineethanol; and,
(R)-4-(2,3-dihydro-1,4-benzodioxin-5-yl)-β-ethyl-1-piperazineethanol and the optical isomers thereof.

* * * * *